US00PP08460P

United States Patent [19]

Knottenbelt

[11] Patent Number: Plant 8,460

[45] Date of Patent: Nov. 16, 1993

[54] APPLE TREE NAMED 'KNOTTENBELT RED'

[75] Inventor: Robert Knottenbelt, Hastings, New Zealand

[73] Assignee: South Pacific Apple Breeders, Hastings, New Zealand

[21] Appl. No.: 811,750

[22] Filed: Dec. 23, 1991

[51] Int. Cl.[5] ..... A01H 5/00

[52] U.S. Cl. ..... Plt./34.1

[58] Field of Search ..... Plt. 34.1

*Primary Examiner*—James R. Feyrer

*Attorney, Agent, or Firm*—Chernoff, Vilhauer, et al.

[57] ABSTRACT

A new variety of apple originating as a seedling found growing on the Coromandel Peninsula near Coromandel, New Zealand. It is unique particularly for its bright, cherry-red, overall skin color, flavor, taste and high dessert quality and otherwise as herein described.

3 Drawing Sheets

SUMMARY OF THE INVENTION

This invention relates to a new variety of apple tree which was discovered as a whole-tree seedling by Mr. Robert Knottenbelt, Poukawa Orchards, R.D. 11, Hastings, New Zealand. Mr. Knottenbelt found his new variety growing as a single tree in a paddock used for pasturing sheep and other domestic farm animals on the Coromandel Peninsula near Coromandel, New Zealand (North Island) in 1972.

Asexual reproduction was successfully accomplished in 1974 at which time second generation trees were grafted. Third generation grafts were placed in 1977.

Trees from both graft generations have borne fruit true-to-type and identical to that produced on the original seedling tree.

Fruit from both generations of trees has been successfully exported from New Zealand to European markets for testing purposes. The bright red fruits arrived at the market in good condition. The skin condition was good with no damage or bruising from handling. Internal condition was crisp, juicy and firm with excellent flavor and texture.

The selection is now recognized as a new apple variety distinguished from all other apple varieties because of its appearance, rich aromatic flavor and taste, and its unique ability to store well over long periods in both common and C.A. storage. After seven months in C.A. storage (2% $O_2$ and 2% $CO_2$) the fruit showed no scald, wilt or storage rot. On immediate cutting and eating, the fruit was crisp, juicy and sweet. After five days at ambient room temperature the fruits were still sound, showed no wilt and possessed a unique sub-acid flavor. The skin is crisp and not tough.

Our new variety is a very precocious bearer of heavy crops of fruit (FIG. 1). For this reason, it becomes necessary to pay close attention to its thinning requirements. Though healthy trees with normal vigor can produce and support heavy crops of large size fruits, tree vigor must be maintained and normal, early fruit thinning is required to produce the large fruit sizes demanded by most fresh world markets. Normal 12–20 cm spacing of king bloom fruits is recommended. The semi-spur type tree has shown itself to grow vigorously and sets early crops if propagated on dwarfing and/or semi-dwarfing rootstocks. Compatibility on all rootstocks tested was found to be good.

The tree is a semi-compact grower. Young one-year-old non-bearing trees growing in an orchard near Parker, Washington USA produced a total average terminal growth of 3.2 meters (320 cm) in the 1992 growing season. This compared to similar one-year-old non-bearing, spur-type red delicious trees which produced an average 2.2 meters (220 cm) of growth in their first year in the orchard and similar one-year-old non-spur Red Fuji trees which produced a total average 3.9 meters (390 cm) of growth in this orchard (Table ).

Table 1

TREE VIGOR (Parker, Washington, USA)

| Variety | Tree Age (yrs in orchard) | Average Grown per Tree (cm)* |
|---|---|---|
| Spur Red Delicious | 1 | 220 |
| Knottenbelt Red | 1 | 320 |
| Red Fuji | 1 | 390 |

* Average of ten trees.

Common bacterial and fungal foliage and back canker diseases such as Anthracnose, Perennial Canker, Nectria Canker Fabraea Leaf Spot, etc., have not been observed. Powders mildew, rust and scab diseases on leaves have made only minimal appearances. Although no controlled experiments have been conducted, close observation indicates that some resistance to these common leaf disease problems is present in areas where evaluations have been and are being conducted.

The new selection has now been fully evaluated and has been grown on a variety of properties (areas and soil types) and under several management techniques. It has performed well under a variety of growing conditions.

Our new variety has not displayed any tendency to biannual bearing. There is some fruit produced even on one-year-old wood. It throws numerous laterals close to the horizontal in all directions.

Trees trained to a vase-shape and allowed to grow naturally without excessive pruning and without bracing of limbs (use of crotch expanders) produce natural crotch angles of about 45 degrees on major scaffold limbs. A dense canopy of leaves can be expected when compared to the number of branches produced because of the new variety's semi-spur type of growth habit. This is true only when compared to non-spur type varieties.

The tree is best developed in an open form to enable maximum light penetration but can be trained on any system and has shown itself to be an easy variety to train.

Our new variety shows no propensity to form water sprouts when trees are allowed to grow naturally. If limbs are mechanically bent to horizontal angles, normal water sprouts will develop. Trees placed on seedling and/or the commonly used clonal rootstocks have shown no tendency to form rootsuckers.

Knottenbelt Red is a large, symmetrical, slightly ribbed (FIG. 4), uniquely flavored apple with overall bright red solid blush color (absent of striping) on a yellow-green background (FIGS. 2, 3, 4 and 5). The bright red blush coloration covers nearly 100 percent of the apple's surface in areas of the tree where ample light penetration occurs. The red overall color develops gradually from mid to late season and overlays the green background color which by late season shows only in the basin and stem cavities or where excessive shading has occurred. Its many medium size angular yellow-orange fruit lenticels are distinctive and characteristic of this new variety (FIG. 5). Fruits produced under Washington, USA growing conditions (FIGS. 4 and 5) are slightly more angular and ribbed in shape and exhibit a more distinct five-pointed crown than those produced on trees growing in New Zealand (FIGS. 2 and 3) where the variety was discovered and early tests were conducted.

The fruits are crisp, juicy and firm with a sweet aromatic flavor evan after long periods of C.A. storage. The skin is only slightly thicker than the Gala cultivar, and is less tough than the skin of Red Delicious. The fruit is not prone to sunburn, surface russet or cracking. Continuing research shows that Knottenbelt Red is slightly subject to bitter pit and internal disorders such as core flush, fungal type rots and other storage pathogens. Some watercore has been observed in stored fruit which was not harvested at its optimum picking date (over-ripe) (Table 2).

Table 2

FRUIT MATURITY DATA

Grower: Irrigated Agricultural Research Station, (Washington State University), Prosser, Washington, USA Variety: Knottenbelt Red

| Date of Testing: October 22, 1991 | | | | | |
|---|---|---|---|---|---|
| Firmness (lbs/kg) | Soluble Solids (%) | Starch Iodine (Golden Delicious Chart) | Color (%) | Size Apples Per Box (standard) | Watercore |
| 16.5 | 13.0 | 2.5 | 90 | 80 | - |
| 18.0 | 16.0 | 3.5 | 85 | 88 | Minor |
| 18.0 | 14.2 | 3.0 | 85 | 88 | - |
| 18.0 | 16.2 | 3.0 | 90 | 80 | - |
| 16.5 | 14.8 | 2.0 | 80 | 80 | - |
| Average: | | | | | |
| 17.4 | 14.8 | 3.0 | - | - | - |

Date of Testing: October 1, 1992 (very early season)

| | | | | | |
|---|---|---|---|---|---|
| 16.75 | 12.6 | 2.5 | 90 | 80 | - |
| 17.0 | 14.0 | 3.0 | 95 | 80 | - |
| 17.5 | 13.2 | 2.5 | 95 | 80 | - |
| 16.5 | 12.6 | 3.0 | 80 | 88 | - |
| 18.0 | 12.0 | 2.0 | 90 | 100 | - |
| Average: | | | | | |
| 17.2 | 12.9 | 2.6 | | | |

The fruit is very uniform in shape in al sizes with a characteristic deep cavity at the calyx end. It sets in clusters of 5 or 6 apples with long stems. The cherry-red color develops mid-to-late February. In New Zealand at or near the site where discovered and tested, the first pick is about Apr. 7, 1990, and the second pick follows about 14 days later. The first two picks harvest about 90% of the crop. Size range has given 85% in 80–125 count with the remaining 15% in the 138–175 range, approximately 30% of fruit fall in 100 count or larger.

Although Knottenbelt Red is not self-incompatible, outside pollen sources will help in setting a full crop in some seasons. All diploid mid-to-late season bloomers such as Red Delicious, Golden Delicious, Gala, Jonathan, etc., will and can serve as a good source of pollen.

DETAILED BOTANICAL DESCRIPTION

Figure 1:
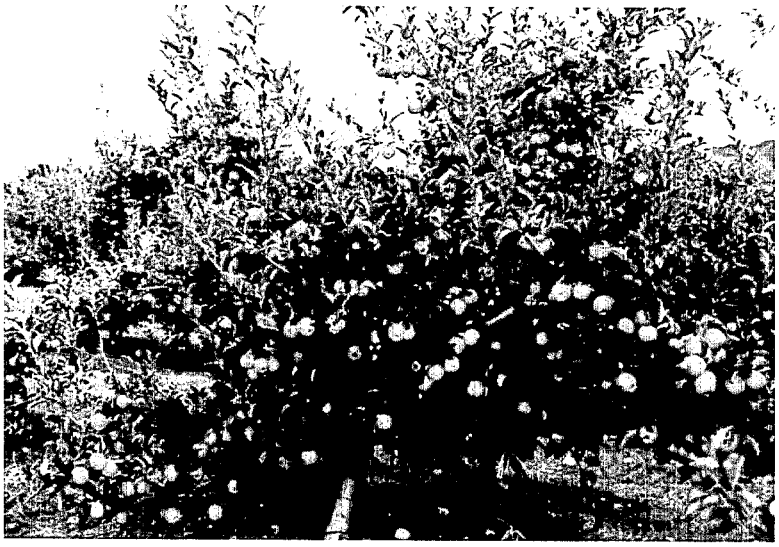
FIG. 1 shows the new variety apple tree bearing fruit and reflects the productivity of the tree of this invention.
Figure 2:
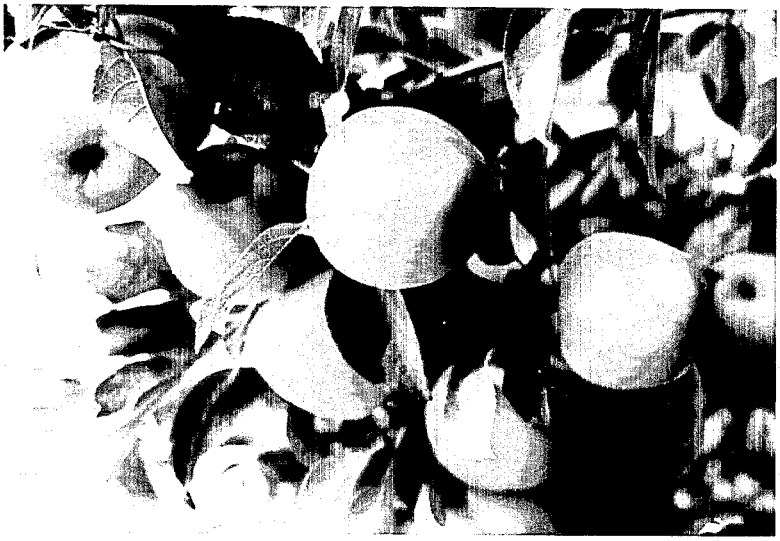
FIG. 2 is a close-up of a branch of the new variety bearing fruit as produced in New Zealand.
Figure 3:
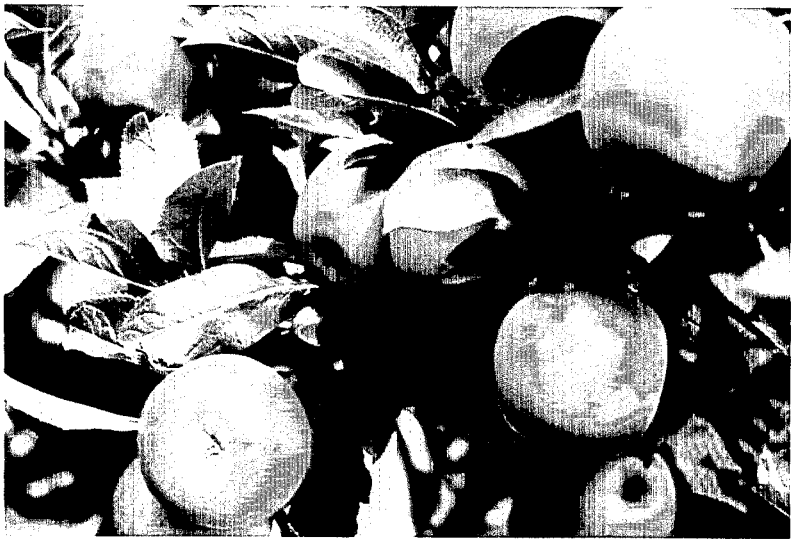
FIG. 3 is a further close-up showing of the new variety depicting the fruit under cultural conditions in New Zealand.
Figure 4:
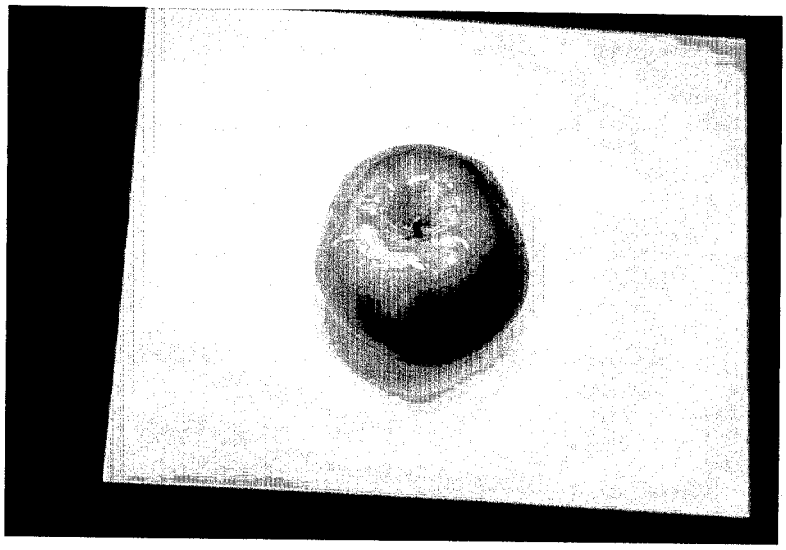
FIG. 4 shows the shape of the fruit of the tree of this invention as being symmetrical and slightly ribbed; the fruit depicted having been produced in Washington State, U.S.A.
Figure 5:
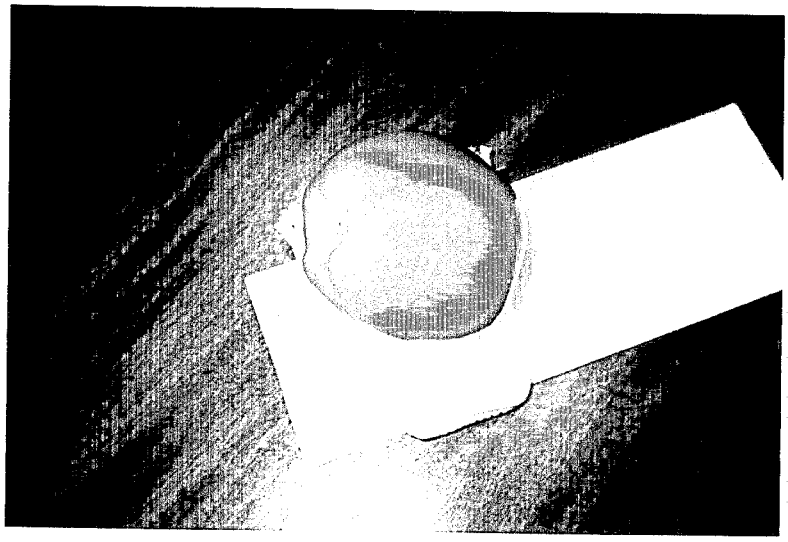
FIG. 5 depicts the ground color and solid red blush coloring of the fruit which is produced by the tree of this invention and shows the characteristic lenticels of the fruit skin; the fruit of this figure being grown in Washington State in the United States.

The accompanying photos show typical specimens of the tree and fuit of our new apple variety depicted in full color. Following is a detailed description of the new variety with color terminology in accordance with the Munsell Color Cascade Chart except where general color terms of ordinary dictionary significance are used.

Parentage: A change seedling.

Localities where grown and observed: Poukawa Orchards, Hastings, New Zealand; Institute of Horticulture and Plant Breeding; Wilhelminadorp, Holland; Lincoln Research Station, South Island; New Zealand; D.S.I.R. Research Station Havelock North, New Zealand; W.S.U. Research Station Mount Vernon, Wash., USA; W.S.U. Research Station, Prosser, Wash., USA; Grower Orchard, Parker, Wash., USA.

Tree: Medium large, moderately vigorous, bushy with dense foliage, spreading.

Ploidy: Diploid.
Trunk: Medium stocky, smooth, dark grown (26-15).
Branches: Medium thick, smooth, much branched, green-brown (23-13).
Lenticels: Large size, many, angular, whitish-grey.
Twigs: Slender, brown with reddish-brown terminal buds.
Dormant fruit buds: Conical, intermediate apex, medium pubescence.
Leaves: Oval, abruptly pointed, medium thick.
*Length.*—Average 7.9 cm.
*Width.*—Average 5.8 cm.
*Color.*—Dark green (19-12), shiny.
*Texture.*—Leathery.
*Position of maximum width.*—At center.
*Margin.*—Coarsely serrate, blunt serrations.
*Hairiness.*—Absent on upper side, medium on lower side.
*Surface configuration.*—Upfolded.
*Shape.*—Abovate.
*Apex.*—Cuspidate.
*Base.*—Rounded.
*Petiole length.*—Medium to long (3.3-4 cm), slender.
*Leaf length/petiole length ratio.*—2.5:1.0.
*Stipule length.*—Long.
*Substipule.*—Absent.
*Pose.*—Upward.
*Veins.*—Some leaves with pink on back side, green on front (veins on leaves growing in shaded areas have a tendency to remain green on back side).
Flowers: Late flowering.
*Overall color.*—Light red (43-8).
*Size.*—Small.
*Shape.*—Flat or slightly uncupped.
*Color of bud.*—Pink.
*Sepal length.*—Short.
*Sepal length/width ratio.*—2.0:1.0.
*Sepal shape.*—Tapered.
*Sepal color.*—Green with light red tips.
*Sepal pose.*—Reflexed.
*Sepal base.*—Obtuse.
*Petal base length/width ratio.*—2.0:1.0.
*Petal arrangement.*—Touching.
*Petal pubescence at base.*—Absent.
*Stamen number.*—Many.
*Stamen pose.*—Upright.
*Stamen color.*—Red.
*Anther shape.*—Typical for apple (2 cells).
*Filament pose.*—Upright.
*Filament length in relation to styles.*—Longer than styles.
*Pollen color.*—Yellow.
*Styles—length in relation to stamens.*—Shorter than stamens.
*Styles—point of fusion: Near base.*
Fruit:
*Maturity when described.*—Eating ripe (specimens described were grown and observed at Hastings, New Zealand).
*Size.*—Large; axial diameter 6.7 cm; horizontal diameter 7.2 cm.
*Length-breadth ratio.*—0.9:1.0.
*General shape.*—Oblong.
*Symmetry.*—Symmetrical.
*Ribs.*—Distinct.
Crowning at eye end.—Medium.
*Basin.*—Abrupt, deep, five-crowned.
*Basin width.*—Medium to wide.
*Basin angle.*—Acute.
*Basin pubescence.*—Present.
*Basin markings.*—None.
*Eye—aperture.*—Closed.
*Eye—length of sepals.*—Long.
*Eye—pose of sepals.*—Partly reflexed.
*Cavity.*—Depth: Deep. Width: Medium. Angle: About 90 degrees. Amount of russet: Moderate. Type of russet: Patchy.
*Stem.*—Protrusion: Much beyond cavity. Length: Long. Thickness: Slender. Distinct swelling at end: Absent.
*Skin.*—Surface texture: Smooth. Bloom: Absent. Greasiness: Slight. Shininess: Moderately shiny. Toughness: Slight. Type of ground color: Green-Yellow (25-10). Intensity of ground color: Medium. Type of over color: Red (42-12). Intensity of over color: Bright red. Form of over color: 75-100%. Number of lenticels: Many, distinct. Size of lenticels: Medium to large. Color of lenticels: Yellow-orange. Russet: Mainly in cavity.
*Flesh.*—Color: Yellowish (24-3). Juiciness: Medium. Firmness: Firm. Texture: Medium. Flavor: Sub-acid. Aroma: Distinct; complex and highly aromatic.
*Calyx tube.*—Length: Long. Width: Medium. Shape: Y-shaped. Position of stamens: Median. Pistil: Persistent. Pubescence of pistil: Moderate. Fusion of styles: United at base.
*Core.*—Size: Small. Position: Median. Distinctness in longitudinal section: Strong. Distinctness in cross section: Narrow.
*Core cell.*—Length: Short. Breadth: Narrow. Aperture: Open (in cross section).
*Number of seed cells.*—Five.
*Seed.*—Size: Medium. Length: 9 mm. Breadth: 5 mm. Length/breadth ratio: 1.8:1.0. Thickness: Flattened. Apex: Acute. Color when dry: Dark brown (32-15). Average number: Ten.
Phenology:
*Time of full flowering.*—About October 16 in Hastings, New Zealand.
*Flowering period.*—About October 12-20 in Hastings, New Zealand.
*Time of Maturity for picking.*—About April 14 in Hastings, New Zealand.
*Fruiting season.*—Late.
Use: Dessert, juice, culinary, fresh market.
Keeping quality: Very good.
Winter hardiness: Hardy where grown.
Precocity: Very precocious (similar to Golden Delicious).
Diseases and pests:
*Apple scab.*—Slightly resistant.
*Mildew.*—Slightly resistant.
*Canker.*—None observed.
*Brown rot.*—None observed.
*Aphids.*—Not tested.
*Green crinkle.*—Tolerant.

What is claimed is:

1. A new variety of apple tree substantially as shown and described herein characterized by its bright red fruit with a rich aromatic flavor and taste, unique ability to store well over long periods of time in both common and controlled atmosphere, and its ability to bear abundantly on an annual basis.

* * * * *

UNITED STATES PATENT AND TRADEMARK OFFICE

CERTIFICATE OF CORRECTION

PATENT NO. : PP 8,460

DATED : November 16, 1993

INVENTOR(S) : Robert Knottenbelt

It is certified that error appears in the above-indentified patent and that said Letters Patent is hereby corrected as shown below:

Column 2, Line 26: delete "Powders" insert --Powdery--

Column 4, Line 52: delete "fuit" insert --fruit--

Column 4, Line 58: delete "change" insert --chance--

Column 4, Line 62: after "Island" delete ";" insert --,--

Column 5, Line 2: delete "grown" insert --brown--

Signed and Sealed this

Eleventh Day of October, 1994

*Attest:*

*Attesting Officer*

Bruce Lehman

BRUCE LEHMAN

*Commissioner of Patents and Trademarks*